(12) United States Patent
Dahl

(10) Patent No.: US 9,433,980 B1
(45) Date of Patent: Sep. 6, 2016

(54) METHOD FOR SUPPLYING CLEAN, SANITIZED DRIVE-THROUGH BANKING CYLINDERS TO A BANK'S CUSTOMERS

(71) Applicant: Terry Dahl, Draper, UT (US)

(72) Inventor: Terry Dahl, Draper, UT (US)

(*) Notice: Subject to any disclaimer, the term of this patent is extended or adjusted under 35 U.S.C. 154(b) by 576 days.

(21) Appl. No.: 13/918,644

(22) Filed: Jun. 14, 2013

Related U.S. Application Data

(60) Provisional application No. 61/659,703, filed on Jun. 14, 2012, provisional application No. 61/662,742, filed on Jun. 21, 2012.

(51) Int. Cl.
*A61L 2/00* (2006.01)
*B08B 9/08* (2006.01)

(52) U.S. Cl.
CPC .................. *B08B 9/0808* (2013.01)

(58) Field of Classification Search
CPC .................................... B08B 9/0808
USPC ............................................. 422/28
See application file for complete search history.

(56) References Cited

U.S. PATENT DOCUMENTS

2011/0027020 A1* 2/2011 Valerino, Sr. ......... B65B 31/046
406/10

OTHER PUBLICATIONS

Template for Pneumatic Tube System Protocol; Swisslog; Jan. 2006; pp. 1-54.*
Bank Cleaning by JaniKing; Jan. 22, 2012; p. 1.*

* cited by examiner

*Primary Examiner* — Kevin Joyner
(74) *Attorney, Agent, or Firm* — Clayton, Howarth & Cannon, P.C.

(57) ABSTRACT

A method of regularly supplying the bank with cleaned and disinfected cylinders and for communicating that fact to the bank's customers is described. The method includes cleaning and sanitizing the cylinders and substituting the cleaned and sanitized cylinders for used cylinders that have not recently been cleaned and sanitized.

14 Claims, 3 Drawing Sheets

METHOD FOR SUPPLYING CLEAN, SANITIZED DRIVE-THROUGH BANKING CYLINDERS TO A BANK'S CUSTOMERS

CROSS-REFERENCE TO RELATED APPLICATIONS

This application claims the benefit of U.S. Provisional Application No. 61/659,703, filed Jun. 14, 2012, and U.S. Provisional Application No. 61/662,742, filed Jun. 21, 2012, both of which are hereby incorporated by reference in their entireties.

STATEMENT REGARDING FEDERALLY SPONSORED RESEARCH OR DEVELOPMENT

Not Applicable.

BACKGROUND

1. The Field of the Invention

This disclosure relates generally to a method for regularly supplying bank customers with cleaned and sanitized cylinders that are used to transport money and other paper items between the customer and the teller stations, as well as cleaning the tubing through which the cylinders travel.

2. Description of Related Art

Drive up banking is a very popular innovation in the banking business. It allows customers the convenience of being able to perform banking transactions with tellers inside the bank without having to leave their automobiles. The transfer of money, deposit slips, identification, and other items necessary to the transaction are transported between the customer and the bank in a closable plastic cylinder that is transported back and forth in a pneumatic tube that communicates with a teller station inside the bank and a drive-up banking station.

One problem with this system is that many people handle these cylinders in the course of a day, and generally do it in conjunction with handling money, one of the dirtiest materials people regularly handle. As a result, they are repositories for all the various microbes that the individuals who handle them may be carrying. Added to this fact is that money, which is another vector for the transmission of microbes, is being handled simultaneously with the cylinders. As a result, the cylinders can be a hotbed of microbes and potential transmitter of disease, similar to grocery store shopping cart handles.

Thus, it would be highly desirable if the drive up banking cylinders and the tube that transmits them could be regularly cleaned and disinfected to reduce their ability to transmit microbes and diseases. From a marketing and customer relations point of view, it would also be good to be able to communicate to a bank's customers that the bank's cylinders are regularly cleaned and disinfected.

SUMMARY

The current disclosure teaches a method for regularly supplying the bank with cleaned and disinfected cylinders and for communicating that fact to the bank's customers.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

At the outset, it should be appreciated that like drawing numbers on different views identify identical structure elements of the disclosure. While the present disclosure is described with respect to what is presently considered to be exemplary embodiments, it is understood that the disclosure is not limited to the disclosed embodiments.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure, which is limited only by the appended claims.

Unless defined otherwise, all technical and scientific terms used herein have the same meaning as commonly understood to one of ordinary skill in the art to which this disclosure belongs. Although any methods, devices or materials similar or equivalent to those described herein can be used in the practice or testing of the disclosure, typical methods, devices, and materials are now described.

Figure 1:
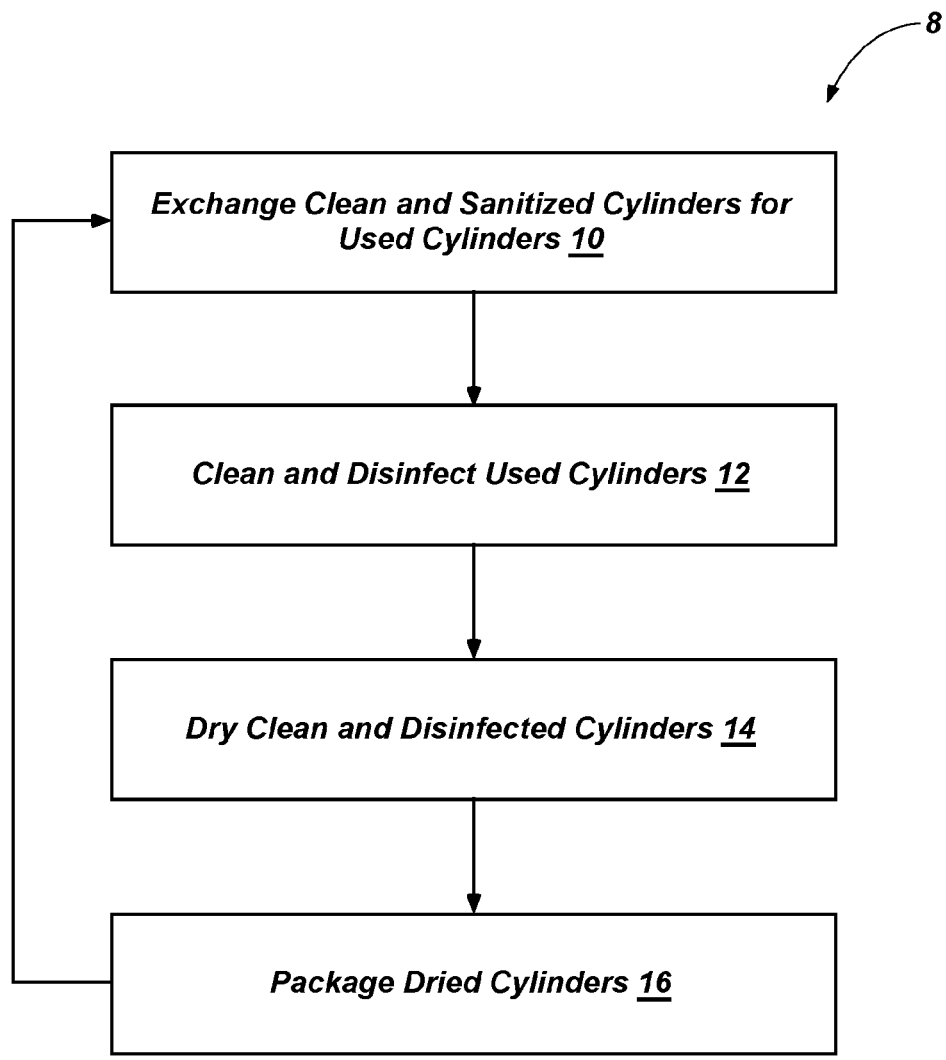
FIG. 1 is a flow chart depicting one illustrative embodiment of the cleaning system.
Figure 2:
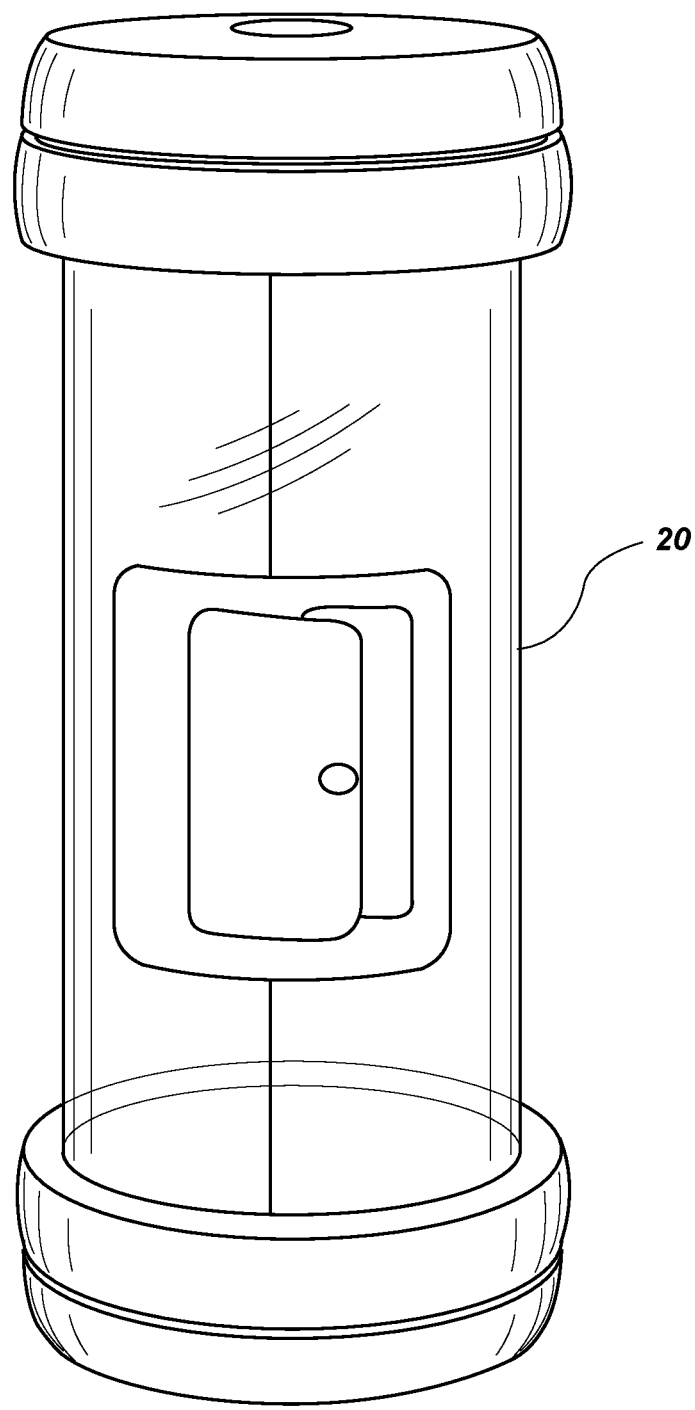
FIG. 2 is a perspective view of a typical drive-up banking cylinder.

FIG. 1 depicts a flow chart showing a set of steps for practicing the method 8. As depicted in FIG. 1, a regularly scheduled pickup and delivery service exchanges 10 the cylinders 20 depicted in FIG. 2 currently in use by the bank with cylinders 20 that have been cleaned and sanitized. The clean and sanitized cylinders 20 may be wrapped in a protective plastic coating or may be boxed or be contained by any other method known to those skilled in the art to protect the newly cleaned and sanitized cylinders 20 from becoming recontaminated.

The collected cylinders 20 are then cleaned and disinfected 12. This may be accomplished by washing the cylinders 20 with a cleaning solution comprising a combination of water at a temperature between 50 and 100 degrees Fahrenheit (10-37.8° C.) and a disinfectant or by water at a temperature high enough to disinfect, as known to those skilled in the art. The water temperature range mentioned herein was selected in view of the materials that are presently used in the manufacture of pneumatic cylinders for drive-up banking use. The temperature should be warm enough to aid in cleaning and sanitizing the cylinders, but not so warm to damage the cylinders. Thus, if materials with different resistances to heat damage were to be used in the construction of the cylinders, then the temperature range should be adjusted accordingly. The disinfectant may comprise soap combined with one or more disinfectants having one or more of the following disinfectant active ingredients: alcohols, aldehydes, oxidizing agents (such as chlorine and oxygen), quaternary ammonium compounds (such as those found in Brody Chemical Brand Disinfectants), phenolics, or other disinfecting compound as known to those skilled in the art. In another embodiment, the disinfectant may comprise dimethyl ethylbenzyl ammonium chloride alkyls and dimethyl benzyl ammonium chloride alkyls. In an alternative embodiment the disinfectant comprises a mixture of the following ingredients: 0.80% fo the following compound— Alkyl (60% C14, 30% C16, 5% C12, 5% C18) dimethyl benzyl ammonium chlorides as an active ingredient; 0.20% of the following compound—Alkyl (68% C12, 32% C14) dimethyl ethylbenzyl ammonium chlorides as an active ingredient; and 98.40% inactive ingredients. In another embodiment, the disinfectant comprises a mixture of the following ingredients: 5.0% fo the following compound—Alkyl (60% C14, 30% C16, 5% C12, 5% C18) dimethyl benzyl ammonium chlorides as an active ingredient; 5.0% of the following compound—Alkyl (68% C12, 32% C14) dimethyl ethylbenzyl ammonium chlorides as an active ingredient; and 90.0% inactive ingredients. In yet another embodiment, the disinfectant comprises a mixture of the following ingredients: Alkyl (60% C14, 30% C16, 5% C12, 5% C18) dimethyl benzyl ammonium chlorides as an active ingredient; Alkyl (68% C12, 32% C14) dimethyl ethylbenzyl ammonium chlorides as an active ingredient; and inactive ingredients.

Other means of sanitizing the cylinders may also be used within the scope of the present invention. An illustrative means of sanitizing the cylinders includes exposure of the cylinders to ionized or non-ionized radiation for a time period effective for inactivating the microbes that may be present. Non-ionized radiation includes UV light, for example.

The washing may be performed by a machine specially designed for the task, a general dishwashing machine, or may be accomplished by hand. The cylinders 20 may be aggregated prior to being cleaned and disinfected by means such as a regularly scheduled delivery route that drops off and picks up cylinders 20 from a number of banks prior to the used cylinders 20 being taken to a centrally located facility for cleaning and disinfecting. After cleaning and disinfecting, the cylinders 20 are dried 14. This can be accomplished by subjecting the cylinders 20 to a dry heat of between 50 and 100 degrees Fahrenheit (10-37.8° C.) until they are dry. In another embodiment, the cylinders 20 may be dried by exposure to the ambient air under circumstances calculated to avoid contamination.

In another embodiment, a vehicle may be outfitted with the equipment needed to clean and disinfect the cylinders 20 on site. In this embodiment, the cylinders 20 are cleaned, disinfected and returned to the bank without having to be transported to a centrally located facility.

After the cylinders 20 are cleaned and dried, the cleaned and dried cylinders 20 are wrapped in plastic, placed in boxes, or contained by any other method known to those skilled in the art to protect the newly cleaned and disinfected cylinders 20 from becoming recontaminated 16. In one illustrative embodiment, the cylinders 20 are contained in a vacuum sealed shrink wrapped plastic.

The sanitized and packaged cylinders 20 are then returned to the bank where they are exchanged for a set of cylinders 20 to be cleaned and disinfected. This cycle may be repeated on a daily, weekly, monthly or other periodic basis.

Figure 3:
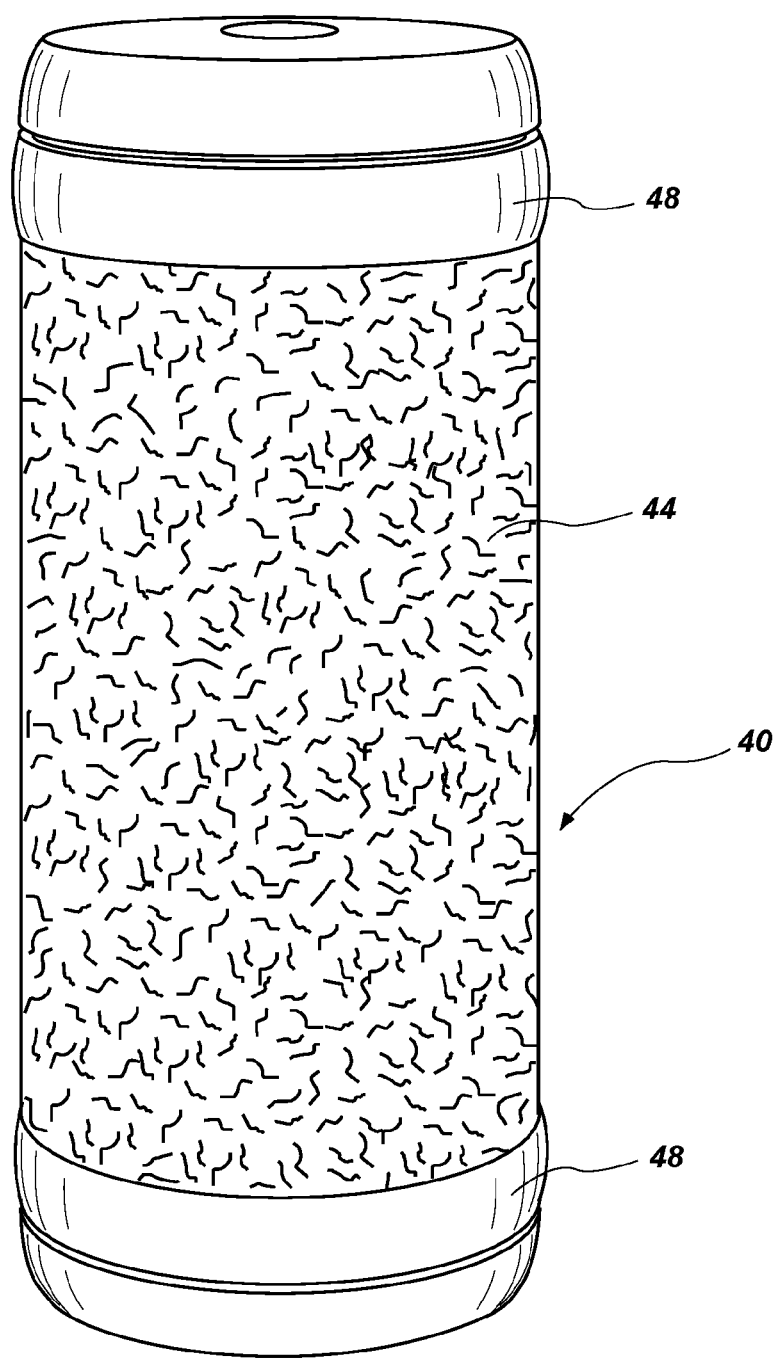
FIG. 3 is a perspective view of a pneumatic tube cleaning device.

In addition to the regular cleaning and disinfecting cycle of the cylinders 20, the method may also include a regular cleaning and disinfecting of the pneumatic transit tube that transports the cylinders 20 between the bank teller stations and the drive-up station. As depicted in FIG. 3, this pneumatic tube may be cleaned by transporting through the transit tube a "pig" 40, which, as used herein, is an object sized and shaped to pass through the transit tube while maintaining contact with the walls of the transit tube. The pig 40 is transported through the transit tube at least once, but may be transported through more than once. In one illustrative embodiment, the pig 40 is sized and shaped to compressibly fit within the transit tube with sufficient tolerances to create a pneumatic seal between the exterior wall of the pig and the interior wall of the transit tube so that the pig can be transported through the transit tube via the transit tube's pneumatic action. In another illustrative embodiment, the pig may comprise a cylinder modified to perform the cleaning function.

The pig may be covered with a terry cloth 44 or other absorbent type covering. The pig 40 may also comprise gaskets 48 similar to those on the standard cylinders 20 to maintain the pneumatic pressure as the pig 40 passes through the pneumatic tube. The pig 40 may be coated with a cleaning solution and/or disinfectant prior to being transported through the transit tube.

In another illustrative embodiment of the invention, the pig may comprise a solid piece of absorbent material of a diameter similar to that of the cylinder 20. This absorbent pig can be soaked with a disinfectant and transmitted through the pneumatic tube to carry out the sanitizing or disinfecting of the inside surface of the pneumatic tube.

In still another illustrative embodiment of the invention, the pig may be comprised of a disposable material and individually wrapped. For example, an absorbent pig may be soaked in a disinfectant and individually sealed and packaged. This pig may be used by opening the packaging, removing the pig, and then transmitting the pig through the pneumatic tube to carry out the sanitizing or disinfecting of the tube.

In yet another illustrative embodiment of the invention, the pig may comprise bristles arranged on the exterior thereof, and the bristles may be soaked in disinfectant and/or cleaning solution. Transmitting the pig through the pneumatic tube would cause the bristles and disinfectant and/or cleaning solution to contact the inner wall of the pneumatic tube, thereby cleaning, disinfecting, or sanitizing the pneumatic tube.

As a final step in this method, a sticker or other printed material may be placed on or near the customer service station informing the customer that the cylinders 20 are regularly cleaned and disinfected. This sticker may contain information regarding the frequency with which the cleaning is accomplished and may contain information regarding the date of the most recent cleaning and disinfecting.

What is claimed is:

1. A method for supplying clean, sanitized cylinders to a bank's customers comprising the steps of:
    exchanging used drive-up teller cylinders for cleaned cylinders;
    washing the used cylinders with a cleaning solution;
    drying the cleaned cylinders;
    packaging the cleaned cylinders to maintain their clean condition; and
    returning the cleaned cylinders to the bank and exchanging the cleaned cylinders for the set of cylinders to be cleaned;
    wherein the method further comprises cleaning a pneumatic transit tube by causing a pig to be transported through the transit tube, wherein the pig is sized and shaped to compressibly fit within the transit tube with tolerances as to create a pneumatic seal between the exterior wall of the pig and the interior wall of the transit tube and wherein the pig is coated with a disinfectant prior to being transported through the transit tube.

2. The method of claim 1, further comprising placing a sticker at or near a customer access point of a drive up teller for informing the customer that the cylinders are cleaned and disinfected.

3. The method of claim 1 wherein the cleaning solution comprises one or more disinfectants having one or more of the following disinfectant active ingredients: alcohols, aldehydes, oxidizing agents (such as chlorine and oxygen), quaternary ammonium compound, phenolics, or other known disinfecting/sanitizing compounds.

4. The method of claim 1 wherein the pig is covered with an absorbent material.

5. The method of claim 1 wherein the cylinders are exchanged at least once a week.

6. A method for supplying clean, sanitized cylinders to a bank's customers comprising the steps of:
   exchanging used drive-up teller cylinders for cleaned cylinders;
   washing the used cylinders with a cleaning solution;
   drying the cleaned cylinders;
   packaging the cleaned cylinders to maintain their clean condition; and
   returning the cleaned cylinders to the bank and exchanging the cleaned cylinders for the set of cylinders to be cleaned;
   wherein the method further comprises placing a sticker at or near a customer access point of a drive up teller for informing the customer that the cylinders are cleaned and disinfected.

7. The method of claim 6, further comprising cleaning a pneumatic transit tube by causing a pig to be transported through the transit tube, wherein the pig is sized and shaped to compressibly fit within the transit tube with tolerances as to create a pneumatic seal between the exterior wall of the pig and the interior wall of the transit tube and wherein the pig is coated with a disinfectant prior to being transported through the transit tube.

8. The method of claim 7 wherein the pig is covered with an absorbent material.

9. The method of claim 6 wherein the cleaning solution comprises one or more disinfectants having one or more of the following disinfectant active ingredients: alcohols, aldehydes, oxidizing agents (such as chlorine and oxygen), quaternary ammonium compound, phenolics, or other known disinfecting/sanitizing compounds.

10. The method of claim 6 wherein the cylinders are exchanged at least once a week.

11. A method for supplying clean, sanitized cylinders to a bank's customers comprising the steps of:
    exchanging used drive-up teller cylinders for cleaned cylinders;
    washing the used cylinders with a cleaning solution;
    drying the cleaned cylinders;
    packaging the cleaned cylinders to maintain their clean condition; and
    returning the cleaned cylinders to the bank and exchanging the cleaned cylinders for the set of cylinders to be cleaned;
    wherein the method further comprises cleaning a pneumatic transit tube by causing a pig to be transported through the transit tube, wherein the pig is covered with an absorbent material and is sized and shaped to compressibly fit within the transit tube with tolerances as to create a pneumatic seal between the exterior wall of the pig and the interior wall of the transit tube and wherein the pig is coated with a disinfectant prior to being transported through the transit tube.

12. The method of claim 11, further comprising placing a sticker at or near a customer access point of a drive up teller for informing the customer that the cylinders are cleaned and disinfected.

13. The method of claim 11 wherein the cleaning solution comprises one or more disinfectants having one or more of the following disinfectant active ingredients: alcohols, aldehydes, oxidizing agents (such as chlorine and oxygen), quaternary ammonium compound, phenolics, or other known disinfecting/sanitizing compounds.

14. The method of claim 11 wherein the cylinders are exchanged at least once a week.

* * * * *